US009611503B2

(12) United States Patent
Suwanakitti et al.

(10) Patent No.: US 9,611,503 B2
(45) Date of Patent: Apr. 4, 2017

(54) *ESCHERICHIA COLI* CELL LINE WITH *THYA* KNOCKOUT AND *FOLA* KNOCKOUT

(75) Inventors: Nattida Suwanakitti, Pathumthani (TH); Sastra Chaotheing, Pathumthani (TH); Yongyuth Yuthavong, Pathumthani (TH); Sumalee Kamchonwongpaisan, Pathumthani (TH)

(73) Assignee: National Science and Technology Development Agency, Pathumthani (TH)

( * ) Notice: Subject to any disclaimer, the term of this patent is extended or adjusted under 35 U.S.C. 154(b) by 119 days.

(21) Appl. No.: 13/996,539

(22) PCT Filed: Feb. 9, 2012

(86) PCT No.: PCT/TH2012/000005
§ 371 (c)(1),
(2), (4) Date: Oct. 9, 2013

(87) PCT Pub. No.: WO2012/108845
PCT Pub. Date: Aug. 16, 2012

(65) Prior Publication Data
US 2014/0295478 A1    Oct. 2, 2014

(30) Foreign Application Priority Data
Feb. 9, 2011    (TH) ................................ 1101000176

(51) Int. Cl.
| A61K 38/00 | (2006.01) |
| C12Q 1/26 | (2006.01) |
| C12N 9/06 | (2006.01) |
| C12N 9/10 | (2006.01) |
| C12N 15/70 | (2006.01) |

(52) U.S. Cl.
CPC ............... *C12Q 1/26* (2013.01); *C12N 9/003* (2013.01); *C12N 9/1007* (2013.01); *C12N 15/70* (2013.01); *C12Y 201/01045* (2013.01)

(58) Field of Classification Search
None
See application file for complete search history.

(56) References Cited

U.S. PATENT DOCUMENTS

| 8,114,650 B2 * | 2/2012 | Weide et al. .......... C12N 9/003 435/189 |
| 2003/0108990 A1 | 6/2003 | Kamper et al. |
| 2009/0099220 A1 | 4/2009 | Yuthavong et al. |

OTHER PUBLICATIONS

Giladi et al. (J. of Bacteriology, vol. 185, pp. 7015-7018, Dec. 2003).*
Levin et al. (Molec. Microbiol., 2004, vol. 54 (3), pp. 1307-1318.*
Ross et al. (Applied & Environmental Microbiology, Jul. 1990, pp. 2164-2169, vol. 56, No. 7).*
Girgis et al. (PLOS ONE, 2009, vol. 4, No. 5, pp. 1-13).*
Wu et al. (Proc. Natl. Acad. Sci., vol. 93, pp. 1130-1134, Feb. 1996).*
Bigas et al. (Vet. Mircobiol., vol. 105, 2005, pp. 223-228).*
Besier et al. (Internal. J. Medical Microbiol., vol. 297, 2007, pp. 217-225).*
Fermer et al. (J. Bacteriol., vol. 179, No. 3, 1997, pp. 831-837).*
Baba et al. (Mol. Systems Biol., 2006, pp. 1-11).*
Salcedo et al. (Molecular and Biochemical Parasitology, vol. 112, 2001, pp. 239-252)*
Bhabha et al. (Nature Structural & Mol. Biol., vol. 20, No. 11, 2013, pp. 1243-52).*
Blum et al. (PNAS, 2000, vol. 97, No. 5, pp. 2241-2246).*
Cortese et al. (Mol. & Biochem. Parasit., vol. 94, 1998, pp. 205-214).*
Miroux et al. (J. Molec. Biol., vol. 260, pp. 289-298, 1996).*
Sulavik et al. (Antimicro. Agents & chemotherapy, 2001, vol. 45, No. 4, pp. 1126-1136).*
Levin et al. (J. of Bacteriology, 2007, vol. 189, nol. 11, pp. 4062-4069).*
Datsenko et al. (PNAS, vol. 97, No. 12, 2000, pp. 6640-6645).*
Wu et al. (PNAS, vol. 93, p. 1130-1134, 1996).*
Bell-Pedersen et al. (JBC, 1991, 173(3), 1193-1200).*
Ulmer et al. (JBC, vol. 190, No. 6, 2008, pp. 2056-2064).*
Girgis et al. (PLOS ONE, May 2009, vol. 4, issue 5, pp. 1-13).*
Griffin et al. (JBC, vol. 280, No. 7, pp. 5456-5467, 2006).*
Illarionova et al. (2002). "Biosynthesis of tetrahydrofolate—stereochemistry of dihydroneopterin aldolase." J Biol Chem. 277:28841-28847.
Sienkiewicz et al. (2008). "Chemical and genetic validation of dihydrofolate reductase-thymidylate synthase as a drug target in African trypanosomes." Mol Microbiol. 69:520-533.
International Preliminary Report on Patentability received for PCT Patent Application No. PCT/TH2012/000005, issued on Jan. 17, 2013, 19 pages.
International Search Report and Written Opinion received for PCT Patent Application No. PCT/TH2012/000005, mailed on Jul. 13, 2012, 8 pages.
Ahrweiler et al., "Construction of a Fol Mutant Strain of *Escherichia Coli* for Use in Dihydrofolate Reductase Mutagenesis Experiments", Journal of Bacteriology, vol. 170, No. 7, Jul. 1988, pp. 3301-3304.
Giladi et al., "FolM, A New Chromosomally Encoded Dihydrofolate Reductase in *Escherichia Coli* ", Journal of Bacteriology, vol. 185, No. 23, Dec. 2003, pp. 7015-7018.

* cited by examiner

*Primary Examiner* — Hope Robinson
(74) *Attorney, Agent, or Firm* — Morrison & Foerster LLP

(57) ABSTRACT

The objective of this invention is to create a double thyA folA knockout *Escherichia coli* (*E. coli*) strain for antifolate screening against DHFR of malaria and other parasites. This strain is used together with a plasmid expressing DHFR-TS from the desired pathogenic organism, which constitutes an anti-DHFR assay against the pathogenic organism of interest. The benefit of this invention is that there is no interference from either host DHFR or trimethoprim, a bacterial DHFR inhibitor. This tool is easy to use and maintain. It provides quick and reliable results as compared with conventional anti-malarial and anti-parasitic assays. This invention should facilitate discovery of new anti-DHFR compounds against malaria and other parasitic diseases.

15 Claims, 5 Drawing Sheets

M: 1Kb+ ladder

1: Plasmid

2: *E. coli* BL21(DE3) digested genomic DNA

3: *E. coli thyA* KO digested genomic DNA

M: 1Kb+ ladder

1: *E. coli thyA* KO digested genomic DNA

2: *E. coli thyA folA* KO digested genomic DNA

E. coli
E. coli thyA folA KO+PfTM4
E. coli thyA folA KO+PfK1
E. coli thyA folA KO+Pv wt
E. coli thyA folA KO+Pv mt
E. coli thyA folA KO+Pm wt E. coli thyAfolA
E. coli thyAfolA KO+Pk wt
E. coli thyAfolA KO+Tb wt
E. coli thyAfolA KO+Tg wt
E. coli thyAfolA KO+Tg mt
E. coli thyAfolA KO+Lm wt

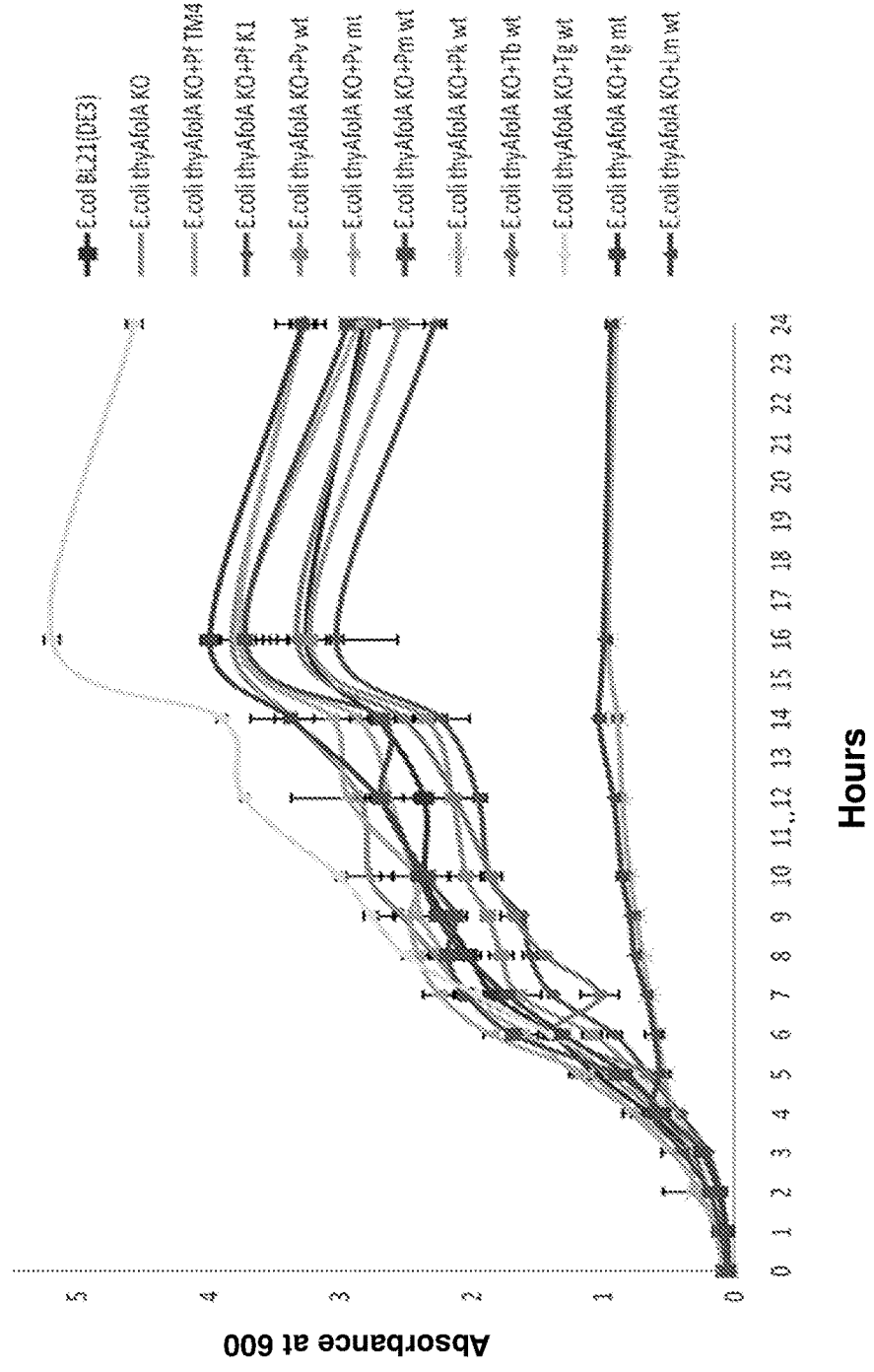

ESCHERICHIA COLI CELL LINE WITH THYA KNOCKOUT AND FOLA KNOCKOUT

TECHNICAL FIELD

Biotechnology with genetic engineering in bacteria and dihydrofolate reductase-thymidylate synthase enzyme inhibition assay

BACKGROUND ART

Malaria is an infectious disease caused by *Plasmodium* parasites. There are 5 species which infect humans:
1. *Plasmodium falciparum* (the most virulent)
2. *Plasmodium vivax*
3. *Plasmodium malariae*
4. *Plasmodium ovale*
5. *Plasmodium knowlesi* (primarily infect monkeys but also humans)

*P. falciparum, P. malariae* and *P. knowlesi* can invade and grow in young and old red blood cells, but *P. vivax* and *P. ovale* can only invade young red cells (reticulocytes). *P. falciparum* and *P. vivax* are the most abundant forms in Thailand. Female *Anopheles dirus* and *Anopheles minimus* are the major mosquito species that transmit malaria in Thailand.

Throughout malaria endemic areas of the World, malaria parasites have developed resistance to most available anti-malarial drugs. There is thus an urgent need for new anti-malarial to counter resistance. Development of anti-malarial drugs is based on empirical screening of natural products and rational drug design against known drug targets. *Plasmodium* dihydrofolate reductase-thymidylate synthase (DHFR-TS) is one of the best characterized targets and has gained a lot of interest as a target for rational drug design. DHFR-TS is a bifunctional enzyme in which the DHFR and TS enzymatic moieties are connected by a junction region (JR). Mutations in the DHFR domain have been found to associate with antifolate resistance. Rational drug design against DHFR is greatly assisted by the availability of several high-resolution crystal structures of this enzyme (including antifolate-resistant variants) in complex with inhibitors such as pyrimethamine, cycloguanil and WR99210. Indeed, this enzyme is also an important drug target for other infectious diseases. In bacteria, the DHFR and TS enzymes are encoded by the folA and thyA genes, respectively. Trimethoprim is an effective inhibitor against the bacterial folA product.

In order to evaluate the anti-malarial activity of compounds, in vitro anti-malarial screening using malaria parasites grown in human red blood cells has been widely employed. The parasites are cultivated in red blood cells with culture media containing human serum. Routine changing of culture media and supplying of new blood cells for the parasites is needed. Moreover, evaluation of drug efficacy requires microscopic, fluorescent, or radioactive methods for enumerating/measuring parasite growth. These requirements are a hindrance to high throughput screening and limit anti-malarial screening to centers with malaria culture systems in place. For target-based anti-malarial screening (which includes antifolates), surrogate models are useful alternatives when malaria culture facilities are not available. Bacterial surrogate models have been employed for antifolate anti-malarial screening in which a folA deficient bacterial cell is complemented by *Plasmodium* DHFR. The bacterial surrogate is made folA deficient either by adding trimethoprim (chemical knockout through inhibition of the host folA enzyme product) or using the PA414 strain, a folA genetic knockout strain. However, anti-malarial drug efficacy evaluated by these methods correlates poorly with conventional anti-malarial screening methods that employ cultured parasites. This may largely be due to off-target interference by trimethoprim and the poor growth rate of PA414, respectively.

This invention entails an *Escherichia coli* strain whose thyA and folA genes were disrupted using genetic knockout. We evaluated the use of this invention as a host for screening DHFR inhibitors against *Plasmodium* malaria and other parasites. This tool, thyA folA KO *E. coli*, is easy and convenient to use. It gives quick and reliable results which correlate well with the conventional anti-malarial screening system. With this tool, it is feasible to perform antifolate assay against malaria and other parasitic diseases in a laboratory with facilities for bacterial cell culture, which more are widely available than parasite culture facilities.

DISCLOSURE OF INVENTION

The aim of this invention is to create a bacterial model suitable for antifolate screening. The invention involves disruption of thyA (thymidylate synthase) and folA (dihydrofolate reductase) genes of *E. coli* BL21(DE3). Please see details below.

1. Creation of a thyA folA Knockout
   1.1 Creation of a thyA Knockout
   There are 3 steps to create a thyA knockout *E. coli:*
   1.1.1 Transforming pKD46 plasmid into *E. coli* BL21 (DE3) by heat shock. This plasmid can assist DNA crossing over. Bacteria transformed with this plasmid need to be cultured at 30 degrees Celsius.
   1.1.2 Introducing the thyA targeting plasmid by electroporation (Bio-Rad electroporation) into *E. coli* BL21 (DE3) containing pKD46 plasmid from step 1.1.1. The thyA targeting plasmid contains a kanamycin resistance gene flanked by 5' and 3' *E. coli* thyA gene fragments (FIG. 1a). The thyA knockout *E. coli* is then selected on LB with kanamycin and supplemented with thymidine at 37 degrees Celsius. This cell is called "*E. coli* thyA KO-KmR". *E. coli* thyA KO-KmR was verified by Southern blot analysis (FIG. 1b) following BglII and SalI digestion to obtain a positive TS band of 2.1 kb.
   1.1.3 Eliminating the kanamycin resistance gene. Plasmid pCP20 was transformed into *E. coli* thyA KO-KmR by the heat shock method. The cells were cultured at 30 degrees Celsius for 16 hours and then at 37 degree Celsius on culture medium without kanamycin. This cell is called "*E. coli* thyA KO"
   1.2 Creation of a Double thyA folA Knockout
   A similar approach was used to create the thyA folA knockout *E. coli* as described in section 1.1. Briefly, plasmid pKD46 was transformed into "*E. coli thyA* KO" obtained from 1.1 by the heat shock protocol. The cells were grown at 30 degrees Celsius ready for disrupting folA by folA targeting plasmid. This plasmid contains a chloramphenicol resistance gene flanked by folA gene 5' and 3' fragments (FIG. 2a). Following electroporation with folA disrupting plasmid, the cells were cultured in the presence of chloramphenicol in media supplemented with thymidine at 37 degrees Celsius. This cell is called "*E. coli* thyA folA KO-CmR". Verification of "*E. coli* thyA folA KO-CmR" by Southern blot analysis of AflII-Nde1 digested bacterial DNA reveals a positive band with DHFR probe at 3.9 kb (FIG. 2b). The chloramphenicol resistance gene was then eliminated by introducing pCP20 plasmid into "*E. coli* thyA folA KO-CmR" by the heat shock method. The cells were cultured at 30 degrees Celsius for 16 hours and then at 37 degrees Celsius on culture medium without chloramphenicol. This cell is called "*E. coli* thyA folA KO"

2. Complementation Assay of *E. coli* thyA folA KO

The role of *E. coli* thyA folA KO as a surrogate host system was examined by introducing plasmids containing dihydrofolate reductase-thymidylate synthase cloned genes from malaria (*P. falciparum, P. vivax, P. malariae* and *P. knowlesi*) and also non-malaria protozoan parasites (*Trypanosoma brucei, Toxoplasma gondii* and *Leishmania major*). The transformed cells were selected on minimal media agar plates without thymidine supplement. The results show that the *E. coli* thyA folA KO transformed with plasmid containing DHFR-TS of malaria or non malaria parasite can grow well on the test plate (FIG. 3). *E. coli* BL21(DE3) and *E. coli* thyA folA KO served as negative controls and could not grow on the same plate.

3. Growth Analysis of *E. coli* thyA folA KO

To test if *E. coli* thyA folA KO can grow normally when complemented with any type of dihydrofolate reductase-thymidylate synthase gene, plasmids containing cloned dihydrofolate reductase-thymidylate synthase genes from malaria and non malaria parasite were transformed into cells. The growth of transformed cells was compared with *E. coli* BL21(DE3) wild type and *E. coli* thyA folA KO when cultured in minimal media and thymidine-supplemented minimal medium, respectively. The results (FIG. 4) show that the growth rates of *E. coli* thyA folA KO, *E. coli* thyA folA KO+Pf TM4, *E. coli* thyA folA KO+Pf K1, *E. coli* thyA folA KO+Pv wt, *E. coli* thyA folA KO+Pv mt, *E. coli* thyA folA KO+Pm wt, *E. coli* thyA folA KO+Tb wt, *E. coli* thyA folA KO+Tg wt, and *E. coli* thyA folA KO+Tg mt are comparable with *E. coli* BL21(DE3) wild type, while *E. coli* thyA folA KO+Pk wt and *E. coli* thyA folA KO+Lm wt grew slower than the others.

4. Using *E. coli* thyA folA KO as a Host for Antifolate Drug Screening 4.1 *E. coli* thyA folA KO as a Host for Antifolate Drug Testing in Malaria and Non Malaria Parasites Pyrimethamine was chosen to test sensitivity of *E. coli* thyA folA KO expressing DHFR-TS from malaria and non malaria parasites. Cells were incubated in minimal media with ampicillin (control) and minimal media with ampicillin and pyrimethamine in 96-well plates with shaking at 37 degrees Celsius for 6 hours. Host cell growth was determined by measuring optical density at 600 nm and the growth compared with enzyme inhibition constant ($K_i$) determined by in vitro biochemical assay using DHFR-TS enzyme purified from heterologous expression in *E. coli* (Table 1).

4.2 *E. coli* thyA folA KO as a Host for Antifolate Drug Testing in *Plasmodium falciparum*

*E. coli* thyA folA KO transformed with plasmids PfTM4 and PfK1 (containing cloned *Plasmodium falciparum* dihydrofolate reductase-thymidylate synthase genes of type TM4, a wildtype, pyrimethamine sensitive strain and type K1, a double mutant pyrimethamine resistant strain, respectively) were tested for antifolate drug sensitivity by culturing transformed cells in minimal media with ampicilin in 96-well plates with shaking at 37 degrees Celsius for 6 hours. The drug inhibition values from testing in *E. coli* thyA folA KO are highly concordant with the values from conventional inhibition assays performed using in vitro malaria culture (FIG. 5). It should be noted that the conventional anti-malarial drug test takes 42 hours, whereas the *E. coli* thyA folA KO testing method uses only 6 hours.

BRIEF DESCRIPTION OF DRAWING

FIG. 1A: thyA gene on *E. coli* BL21(DE3) chromosome was deleted by double-crossover homologous recombination with a linear thyA-knockout plasmid. The plasmid contains a kanamycin resistance gene flanked by 5' and 3' homologous sequences of the thyA gene. Following transformation, thyA knock-out kanamycin resistant *E. coli* was obtained. The kanamycin resistance, gene was then eliminated by the function of pCP20 to obtain "*E. coli* thyA KO" strain free of antibiotic resistance gene. BglII and SalI restriction sites and TS probing site (thick line) used for Southern blot analysis are depicted. FIG. 1B: Southern blot analysis of *E. coli* thyA KO genomic DNA digested with BglII and SalI and hybridized with TS probe. Band sizes of 4.8 kb for *E. coli* BL21(DE3) in lane 2 and 2.1 kb for *E. coli* thyA KO in lane 3 were detected as expected.

FIG. 2A: folA gene on *E. coli* BL21(DE3)thyA KO chromosome was deleted by a double-crossover homologous recombination with a linear folA knockout plasmid. The plasmid contains a chloramphenicol resistance gene flanked by 5' and 3' homologous sequences of the folA gene. Following transformation, thyA folA knockout chloramphenicol resistant *E. coli* was obtained. The chloramphenicol resistance gene was then eliminated by the function of pCP20 to obtain *E. coli* thyAfolA KO strain free of antibiotic resistance gene. AflII and NdeI restriction sites and DHFR probing site (thick line) used for Southern blot analysis are depicted. FIG. 2B: Southern blot analysis of *E. coli* thyA folA KO genomic DNA digested with AflII and NdeI and hybridized with DHFR probe. Band sizes of 5.8 kb for *E. coli* BL21(DE3) in lane 2 and 3.9 kb for *E. coli* thyAfolA KO in lane 3 were observed as expected.

Figure 1A:
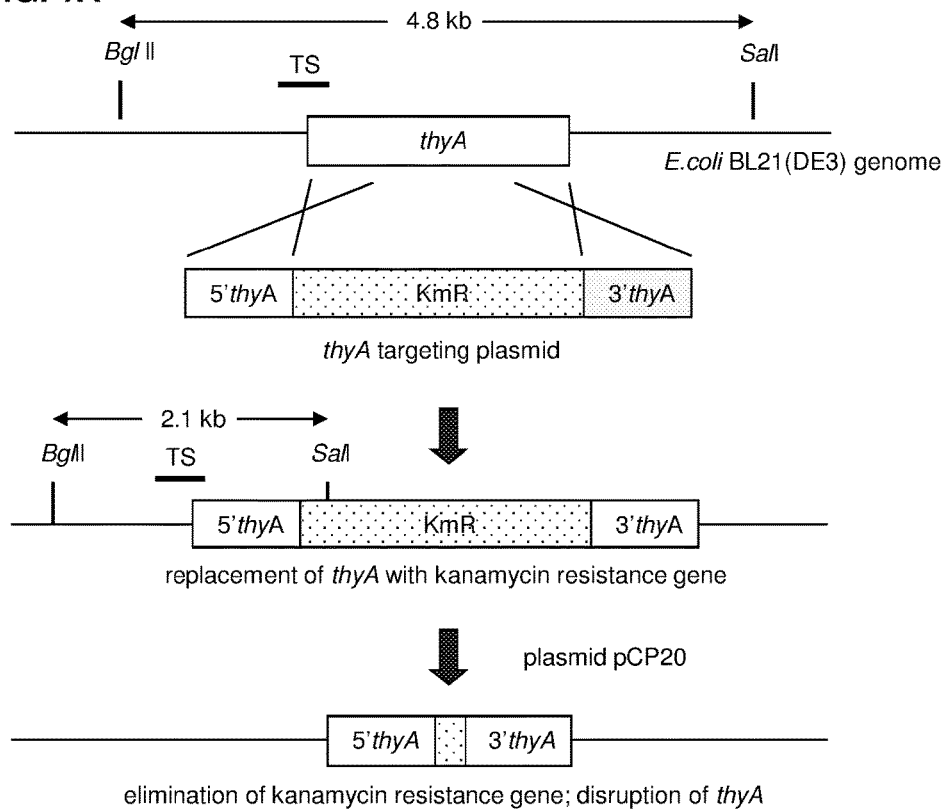
FIG. 1A-B: Invention steps for creating a thyA knockout *E. coli* strain by a double crossover strategy.
Figure 1B:
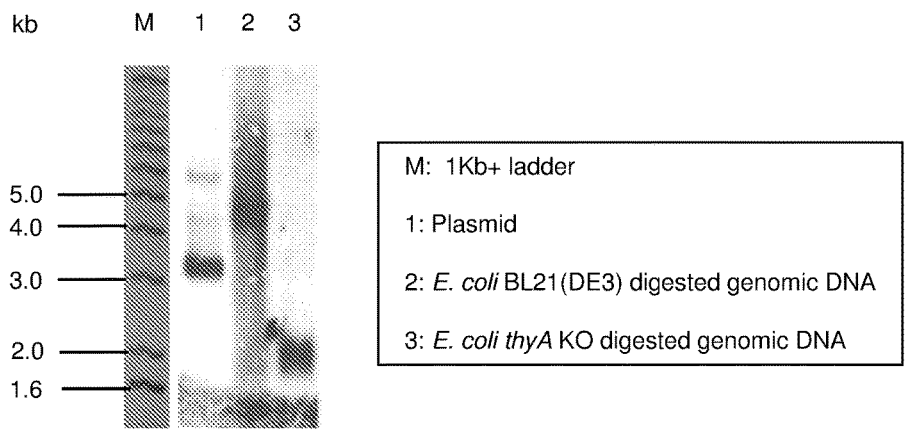
Figure 2A:
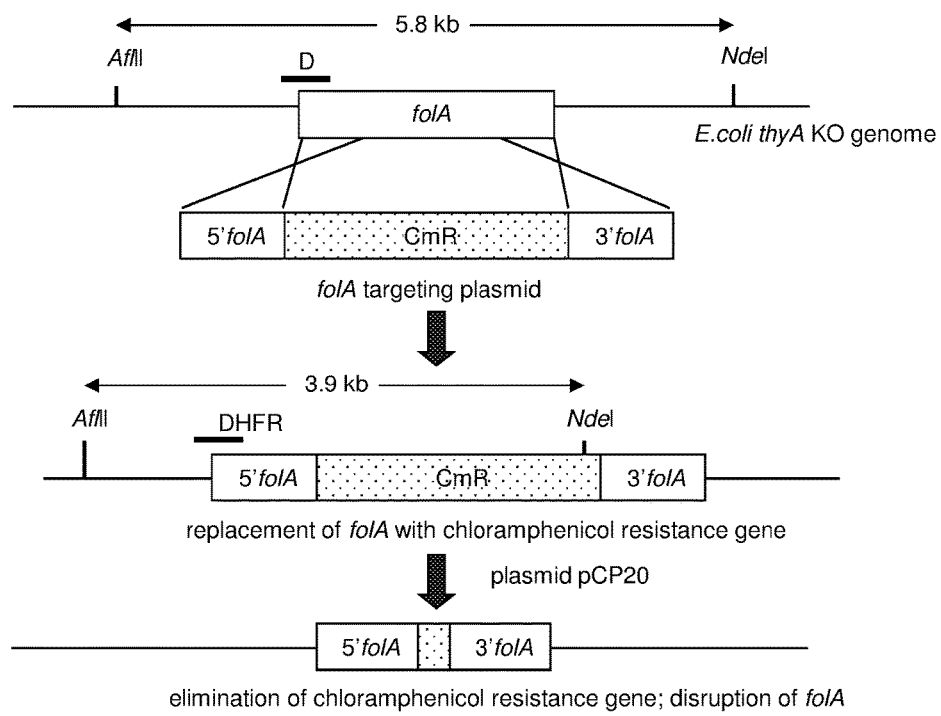
FIG. 2A-B Invention steps for creating a thyA folA knockout *E. coli* strain by a double crossover strategy
Figure 2B:
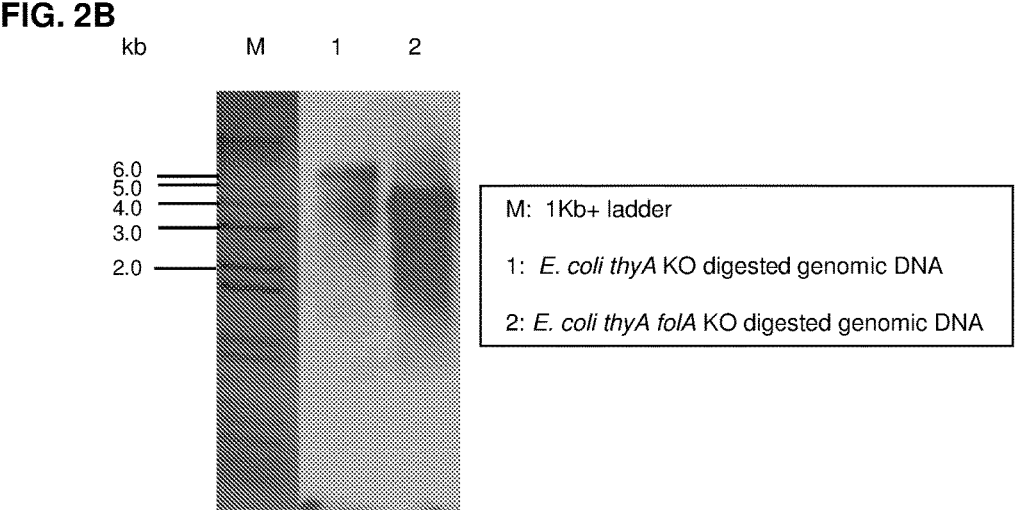
Figure 3:
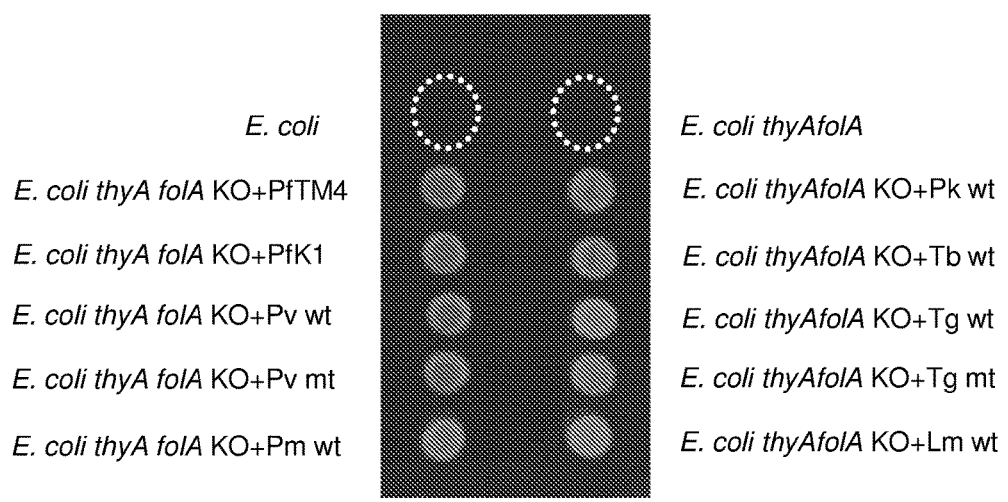
FIG. 3 Evaluation of the invention. Complementation assay of *E. coli* thyA folA KO was performed using plasmids expressing DHFR-TS from malaria and non malaria parasites.

*E. coli* BL21(DE3) is *E. coli* BL21(DE3) wild type

*E. coli* thyA folA KO+pET17b is *E. coli* thyA folA KO with control plasmid pET17b (no cloned dhfr-ts gene)

*E. coli* thyA folA KO+Pf TM4 is *E. coli* thyA folA KO with pET17b plasmid containing dhfr-ts from *Plasmodium falciparum* TM4 (a wildtype, pyrimethamine sensitive strain)

*E. coli* thyA folA KO+PfK1 is *E. coli* thyA folA KO with pET17b plasmid containing dhfr-ts from *Plasmodium falciparum* K1 strain (a double mutant pyrimethamine resistant strain)

*E. coli* thyA folA KO+Pv wt is *E. coli* thyA folA KO with pET17b plasmid containing dhfr-ts from *Plasmodium vivax* (a wildtype, pyrimethamine sensitive strain)

*E. coli* thyA folA KO+Pv mt is *E. coli* thyA folA KO with pET17b plasmid containing dhfr-ts from *Plasmodium vivax* sp21 strain (a double mutant pyrimethamine resistant strain)

*E. coli* thyA folA KO+Pm wt is *E. coli* thyA folA KO with pET17b plasmid containing dhfr-ts from *Plasmodium malariae* (a wildtype strain)

*E. coli* thyA folA KO+Pk wt is *E. coli* thyA folA KO with pET17b plasmid containing dhfr-ts from *Plasmodium knowlesi* (a wildtype strain)

E. coli thyA folA KO+Tb wt is E. coli thyA folA KO with pET17b plasmid containing dhfr-ts from *Trypanosoma brucei* (a wildtype strain)

E. coli thyA folA KO+Tg wt is E. coli thyA folA KO with pET17b plasmid containing Tgdhfr-ts from *Toxoplasma gondii* (a wildtype strain)

E. coli thyA folA KO+Tg mt is E. coli thyA folA KO with pET17b plasmid containing dhfr-ts from *Toxoplasma gondii* (a double mutant pyrimethamine resistant strain)

E. coli thyA folA KO+Lm wt is E. coli thyA folA KO with pET17b plasmid containing dhfr-ts from *Leishmania major*

FIG. 4 Growth curves of E. coli thyA folA KO strain transformed with plasmid expressing DHFR-TS of malaria and non malaria parasites in minimal media without thymidine supplement. For comparison, E. coli thyA folA KO free of plasmid was also cultured in thymidine-supplemented media.

E. coli BL21(DE3) is E. coli BL21(DE3) wild type

E. coli thyA folA KO+pET17b is E. coli thyA folA KO with pET17b plasmid

E. coli thyA folA KO+Pf TM4 is E. coli thyA folA KO with pET17b plasmid containing dhfr-ts *from Plasmodium falciparum* TM4 (a wildtype, pyrimethamine sensitive strain)

E. coli thyA folA KO+Pf K1 is E. coli thyA folA KO with pET17b plasmid containing dhfr-ts from *Plasmodium falciparum* K1 strain (a double mutant pyrimethamine resistant strain)

E. coli thyA folA KO+Pv wt is E. coli thyA folA KO with pET17b plasmid containing dhfr-ts from *Plasmodium vivax* (a wildtype pyrimethamine sensitive strain)

E. coli thyA folA KO+Pv mt is E. coli thyA folA KO with pET17b plasmid containing dhfr-ts from *Plasmodium vivax* sp21 strain (a double mutant pyrimethamine resistant strain)

E. coli thyA folA KO+Pm wt is E. coli thyA folA KO with pET17b plasmid containing dhfr-ts from *Plasmodium malariae* (a wildtype strain)

E. coli thyA folA KO+Pk wt is E. coli thyA folA KO with pET17b plasmid containing dhfr-ts from *Plasmodium knowlesi* (a wildtype strain)

E. coli thyA folA KO+Tb wt is E. coli thyA folA KO with pET17b plasmid containing dhfr-ts from *Trypanosoma brucei* (a wildtype strain)

E. coli thyA folA KO+Tg wt is E. coli thyA folA KO with pET17b plasmid containing Tgdhfr-ts from *Toxoplasma gondii* (a wildtype strain)

E. coli thyA folA KO+Tg mt is E. coli thyA folA KO with pET17b plasmid containing dhfr-ts from *Toxoplasma gondii* (a double mutant, pyrimethamine resistant strain)

E. coli thyA folA KO+Lm wt is E. coli thyA folA KO with pET17b plasmid containing dhfr-ts from *Leishmania major*

Figure 5A:
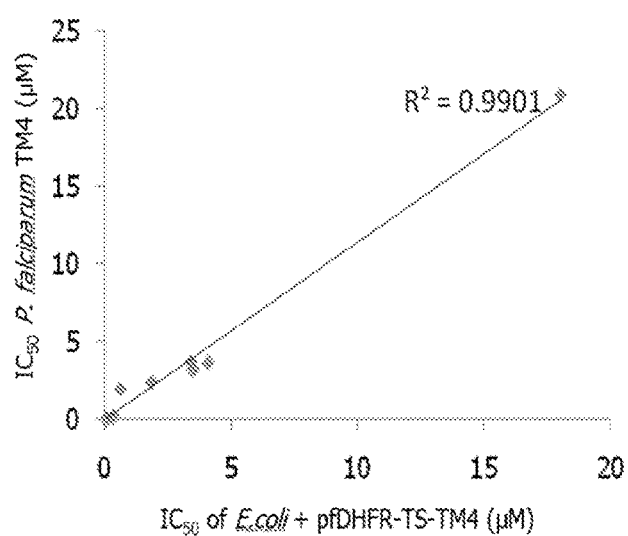
Figure 5B:
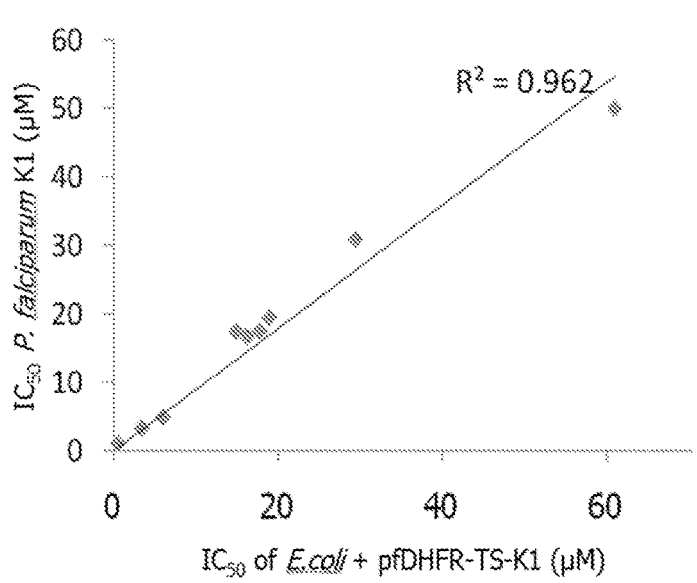

FIG. 5 Correlations of antifolate $IC_{50}$ values obtained from E. coli thyA folA KO strain expressing PfDHFR-TS (x-axes) and those from conventional anti-malarial screening using in vitro malaria culture (y-axes). Two *P. falciparum* strains, TM4 (wildtype, pyrimethamine sensitive) and K1 (double mutant, pyrimethamine resistant) were tested. ($IC_{50}$ is the concentration of inhibitor that inhibits 50% bacterial/parasite growth)

Table 1 Summary of 50% inhibitory concentration of pyrimethamine against E. coli thyA folA KO expressing DHFR-TS from malaria and non malaria parasite and drug susceptibility.

| E. coli thyA folA KO transformed with DHFR-TS containing plasmid | Pyrimethamine | | |
|---|---|---|---|
| | $IC_{50}$ (μM) | $K_i$ DHFR (nM) | Interpretation |
| E. coli thyA folA KO + Pf TM4 | 0.07 ± 0.01 | 0.60 ± 0.20 | sensitive |
| E. coli thyA folA KO + Pf K1 | 31.93 ± 0.16 | 53.90 ± 6.50 | resistant |
| E. coli thyA folA KO + Pv wt | 3.08 ± 0.33 | 0.21 ± 0.03 | sensitive |
| E. coli thyA folA KO + Pv mt | >100 | 3.04 ± 0.44 | resistant |
| E. coli thyA folA KO + Pm wt | 0.77 ± 0.22 | 0.54 ± 0.06 | sensitive |
| E. coli thyA folA KO + Tb wt | >100 | 14.57 ± 0.59 | resistant |
| E. coli thyA folA KO + Tg wt | >100 | 13.02 ± 1.87 | resistant |
| E. coli thyA folA KO + Tg mt | >100 | 48.45 ± 7.97 | resistant |
| E. coli thyA folA KO + Lm wt | >100 | 200.33 ± 59 | resistant |

BEST MODE FOR CARRYING OUT THE INVENTION

As described above in disclosure of invention section.

INDUSTRIAL APPLICABILITY

As described above in disclosure of invention section.

The invention claimed is:

1. An *Escherichia coli* (*E. coli*) cell line in which its thymidylate synthase (thyA) and dihydrofolate reductase (folA) genes have been disrupted by genetic knock out of the thy A and folA genes (*E. coli* thyA folA KO), wherein antibiotic resistance genes used to create the genetic knockout have been functionally eliminated, and wherein said cell comprises a parasite dihydrofolate reductase-thymidylate synthase (DHFR-TS) gene for heterologous expression of a parasite DHFR-TS enzyme.

2. The cell line of claim 1, wherein said cell is *E. coli* type BL21(DE3).

3. The cell line of claim 1, wherein said parasite gene is of a parasite genus selected from the group consisting of *Plasmodium, Trypanosoma, Toxoplasma*, and *Leishmania*.

4. The cell line of claim 1, wherein said parasite DHFR-TS gene is of a *Plasmodium* species selected from the group consisting of *Plasmodium falciparum, Plasmodium vivax, Plasmodium malariae*, and *Plasmodium knowlesi*.

5. A method for identifying a dihydrofolate reductase-thymidylate synthase (DHFR-TS) inhibitor, comprising:
a) growing the *E. coli* cell line of claim 1 in the presence and absence of a candidate drug in media;
b) identifying the candidate drug as a DHFR-TS inhibitor when the cell line grows more quickly in the absence as compared to the presence of the candidate drug.

6. The method of claim 5, wherein the media does not comprise a thymidine supplement.

7. The method of claim 5, wherein step a) comprises growing the cell line for from 6 to 24 hours.

8. The method of claim 5, wherein step a) comprises growing the cell line for from 6 to 12 hours.

9. The method of claim 5, further comprising measuring one or both of dihydrofolate reductase activity and thymidylate synthase activity of the parasite DHFR-TS enzyme in the presence and absence of the candidate drug.

10. The method of claim 9, further comprising identifying the candidate drug as a dihydrofolate reductase (DHFR) inhibitor when the dihydrofolate reductase activity of the parasite DHFR-TS enzyme is higher in the absence as compared to the presence of the candidate compound.

11. The method of claim 9, further comprising identifying the candidate drug as a thymidylate synthase (TS) inhibitor when the thymidylate synthase activity of the parasite DHFR-TS enzyme is higher in the absence as compared to the presence of the candidate compound.

12. The cell line of claim 1, wherein the parasite dihydrofolate reductase-thymidylate synthase (DHFR-TS) gene is present on a plasmid.

13. The cell line of claim 1, wherein the heterologous expression of the parasite DHFR-TS enzyme permits the cell line to grow on minimal media without thymidine supplementation.

14. The cell line of claim 1, wherein the cell line is sensitive to one or both of kanamycin and chloramphenicol.

15. The method of claim 5, wherein the cell line is sensitive to one or both of kanamycin and chloramphenicol.

* * * * *